(12) United States Patent
Chokshi et al.

(10) Patent No.: US 10,150,733 B2
(45) Date of Patent: Dec. 11, 2018

(54) AMIDOHETEROARYL AROYL HYDRAZIDE ETHYNES

(71) Applicant: SUN PHARMA ADVANCED RESEARCH COMPANY LTD., Mumbai (IN)

(72) Inventors: Hemant Ashvinbhai Chokshi, Baroda (IN); Sabbirhusen Yusufbhai Chimanwala, Baroda (IN); Varun Anilkumar Mehta, Baroda (IN); Prabal Sengupta, Baroda (IN); Chitturi Trinadha Rao, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

(21) Appl. No.: 15/574,967

(22) PCT Filed: May 18, 2016

(86) PCT No.: PCT/IN2016/050142
§ 371 (c)(1),
(2) Date: Nov. 17, 2017

(87) PCT Pub. No.: WO2016/185490
PCT Pub. Date: Nov. 24, 2016

(65) Prior Publication Data
US 2018/0127372 A1 May 10, 2018

(30) Foreign Application Priority Data
May 18, 2015 (IN) .......................... 1953/MUM/2015

(51) Int. Cl.
*C07D 213/75* (2006.01)
*C07D 401/12* (2006.01)
*C07B 43/06* (2006.01)

(52) U.S. Cl.
CPC ............ *C07D 213/75* (2013.01); *C07B 43/06* (2013.01); *C07D 401/12* (2013.01)

(58) Field of Classification Search
CPC .................................................... C07D 213/75
USPC ........................................................ 546/306
See application file for complete search history.

(56) References Cited

U.S. PATENT DOCUMENTS 9,024,021 B2 * 5/2015 Sengupta ............. C07D 213/56
544/236

FOREIGN PATENT DOCUMENTS

WO 2007/133560 A2 11/2007
WO 2013/127729 A1 9/2013

OTHER PUBLICATIONS

Written Opinion of the International Searching Authority of PCT/IN2016/050142 dated Aug. 25, 2016.
International Search Report of PCT/IN2016/050142 dated Aug. 25, 2016.

* cited by examiner

*Primary Examiner* — Patricia L Morris
(74) *Attorney, Agent, or Firm* — Sughrue Mion, PLLC

(57) ABSTRACT

The present invention relates to novel amidoheteroaryl aroyl hydrazide ethynes as tyrosine kinase inhibitors, process of preparation thereof, and use of the compounds for preparation of pharmaceutical compositions in the therapeutic treatment of disorders related to tyrosine kinases in humans.

4 Claims, No Drawings

AMIDOHETEROARYL AROYL HYDRAZIDE ETHYNES

RELATED APPLICATIONS

This application claims the benefit of Indian Patent Application no. 1953/MUM/2015 filed on May 18, 2015 which is hereby incorporated by reference.

FIELD OF INVENTION

The present invention relates to novel amidoheteroaryl aroyl hydrazide ethynes as tyrosine kinase inhibitors, process of preparation thereof, and use of the compounds for preparation of pharmaceutical compositions in the therapeutic treatment of disorders related to tyrosine kinases in humans.

BACKGROUND OF THE INVENTION

Protein tyrosine kinases are currently recognized as important molecular targets for drug development in the treatment of several disorders, particularly in the treatment of proliferative disorders. Dysregulation of tyrosine kinase activity has emerged as a major mechanism by which cancer cells evade normal physiological constraints on growth, proliferation and survival. One of the key focus areas in anti-TK drug discovery is the design and development of small molecules that can directly inhibit catalytic activity of the kinase by interfering with the binding of ATP or substrates. An important advantage of TK-directed therapy is the possibility to perform pharmacodynamic studies that correlate inhibition of the targeted TK in cancer cells with clinical responses to the drug.

Classical tyrosine kinase inhibitors, which are predominantly the Bcr-Abl kinase inhibitors that are currently in clinical use, are described in the following patent literature:

U.S. Pat. No. 5,521,184 (the '184 patent): Exemplifies 4-[(Methyl-1-piperazinyl)methyl]-N-[4-methyl-3-[[4-(3-pyridinyl)-2-pyrimidinyl]amino]-phenyl]benzamide methanesulfonate (Imatinib mesylate, Gleevec®)

U.S. Pat. No. 7,169,791 (the '791 patent): Exemplifies 4-Methyl-N-[3-(4-methyl-imidazol-1-yl)-5-trifluoromethyl-phenyl]-3-(4-pyridin-3-yl-pyrimidin-2-ylamino)-benzamide (Nilotinib, Tasigna®)

U.S. Pat. No. 6,596,746 (the '746 patent): Exemplifies N-(2-chloro-6-methylphenyl)-2-(6-(4-(2-hydroxyethyl)piperazin-1-yl)-2-methylpyrimidin-4-ylamino) thiazole-5-carboxamide (Dasatinib, Sprycel®)

While the second generation TK inhibitors in clinic viz. nilotinib and dasatinib have provided additional treatment option to patients who have developed resistance to imatinib, there are certain shortcomings with regard to their side effects. Particularly in the case of dasatinib, the increased potency may be associated with untoward off-target toxicities, which probably relate to their inhibitory activity against a broader range of protein kinases such as Kit, PDGFR and ephrin receptor (EphA2) tyrosine kinases which are directly implicated in haematopoiesis, control of tissue interstitial-fluid pressure and angiogenesis. These effects may provide the physiological explanation for some of the toxicities associated with dasatinib therapy such as myelosuppression and pleural effusion. Besides, treatment with highly potent Abl kinase inhibition has potential for the development of cardiotoxicity in patients with CML.

Studies have shown that patients taking imatinib develop resistance to the drug during the course of therapy. Recent research has provided a better understanding of the mechanism of resistance which led to the development of second generation TK inhibitors. Although the second generation TK inhibitors in clinic provide treatment alternatives for patients who develop resistance to imatinib therapy, the prognosis for the patients having T315I mutation is not good since none of these currently marketed therapies are effective. There is thus an unmet medical need with regard to treatment of patients having the T315I mutation. Omacetaxine (homoharringtonine) is approved by the FDA for CML patients with T315I. However, it is an intravenous drug with a non-specific mechanism of action. Ariad Compound Ponatinib (AP24534, U.S. Pat. No. 8,114,874) is also approved by US FDA but has a boxed warning for risk-threatening blood clots and severe narrowing of blood vessels. Other drug candidates in clinical phase include the Deciphera compound DCC-2036 (PCT Publication No. WO 2008/046003). The present applicant previously reported novel diarylacetylene hydrazides as tyrosine kinase inhibitors published as WO 2012/098416 A1.

The current invention describes novel amidoheteroaryl aroyl hydrazide ethynes containing compounds which are not only potent inhibitors of Abl tyrosine kinase but also on its mutant versions.

SUMMARY

The present invention provides compounds of Formula I

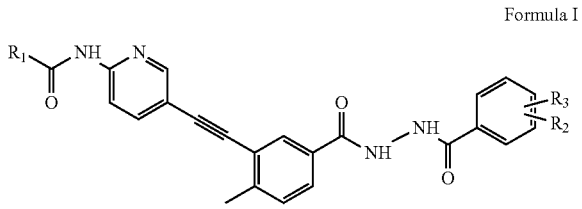

Formula I and pharmaceutically acceptable salts thereof wherein, $R_1$ is selected from —$C_{3-6}$ cycloalkyl, —$C_{1-6}$ alkyl-$NH_2$, —$C_{1-6}$ alkyl-NH($C_{1-6}$ alkyl), —$C_{1-6}$ alkyl-N($C_{1-6}$ alkyl)$_2$, —$C_{3-6}$ alkenyl, —$C_{3-6}$ alkynyl, —$C_{1-6}$ alkyl, —C(O) heterocyclyl, heterocyclyl-$C_{1-6}$ alkyl, —$C_{1-6}$ haloalkyl, —NH ($C_{3-6}$ cycloalkyl) and heterocyclyl wherein heterocyclyl is 5-6 membered non-aromatic ring containing 1 to 2 heteroatom individually selected from N, O or S;

$R_1$ is optionally substituted with one or more group independently selected from —$C_{1-4}$ alkyl, halogen, CN, NH($C_{1-6}$ alkyl), N($C_{1-6}$ alkyl)$_2$, $NH_2$ and hydroxy;

$R_2$ and $R_3$ are individually selected from a group of hydrogen, halogen, —$C_{1-4}$ alkyl, —$C_{1-4}$ haloalkyl, heterocyclyl-$C_{1-4}$ alkyl and heteroaryl wherein, heterocyclyl is 5-6 membered non-aromatic ring containing 1 to 2 heteroatom independently selected from N, O or S and is unsubstituted or substituted with —$C_{1-4}$ alkyl and heteroaryl is 5-6 membered aromatic ring containing 1 to 2 heteroatom independently selected from N, O or S and is unsubstituted or substituted with —$C_{1-4}$ alkyl.

The compounds of the present invention are potent inhibitors of Abl tyrosine kinase including its mutants, and can be used for treating the disease which responds to an inhibition of a tyrosine kinase, especially a neoplastic disease.

Definition

The following are definitions of the terms used in this specification. The initial definition provided for a group or term herein applies to that group or term throughout the present specification, individually or as part of another group, unless otherwise indicated. The term "cycloalkyl" denotes a non-aromatic mono-, or multicyclic ring system of 3 to about 13 carbon atoms. Monocyclic rings include, but are not limited to cylcopropyl, cyclobutyl, cyclopentyl and cyclohexyl. Examples of simple multicyclic cycloalkyl groups include perhydronapththyl, perhydroindenyl etc; bridged multicyclic groups include adamantyl and norbornyl etc, and spriromulticyclic groups for e.g., spiro(4,4)non-2-yl. Unless set forth or recited to the contrary, all cycloalkyl groups described or claimed herein may be substituted or unsubstituted.

The term "alkyl" refers to a hydrocarbon chain radical that includes solely carbon and hydrogen atoms in the backbone, either linear or branched, having from one to eight carbon atoms, both inclusive, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain, linear or branched having 1 to 6 carbon atoms, both inclusive. Unless set forth or recited to the contrary, all alkyl groups described or claimed herein may be, substituted or unsubstituted.

The term "alkenyl" refers to a hydrocarbon chain containing from 3 to 6 carbon atoms, both inclusive and including at least one carbon-carbon double bond which is not in the 1 position, and may have (E) or (Z) configuration. Non-limiting examples of alkenyl groups include 2-propenyl (allyl), 2-methyl-2-propenyl, and (Z)-2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond which is not in the 1 position, and having 3 to about 8 carbon atoms, both inclusive (with radicals having 3 to about 6 carbon atoms being preferred). Non-limiting examples of alkynyl groups include 2-propynyl and 3-butynyl. Unless set forth or recited to the contrary, all alkynyl groups described or claimed herein may be straight chain or branched, substituted or unsubstituted.

The term "heterocyclic ring" or "heterocyclyl" unless otherwise specified refers to substituted or unsubstituted non-aromatic 5 to 10 membered ring, preferably 5-6 membered ring, which consists of carbon atoms and from one to five heteroatoms selected from nitrogen, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quarternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The terms "halogen" or "halo" means fluorine, chlorine, bromine or iodine. Similarly, "haloalkyl" or "haloalkoxy" refers to an alkyl or alkoxy group substituted with one or more halogen atoms.

The term "heteroaryl" unless otherwise specified refers to substituted or unsubstituted 5 to 14 membered aromatic heterocyclic ring radicals with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolinyl, isoquinolinyl, thiadiazolyl, indolizinyl, acridinyl, phenazinyl, imidazo[1,2-a]pyridyl, imidazo[1,2-a]pyridine and phthalazinyl. Unless set forth or recited to the contrary, all heteroaryl groups described or claimed herein may be substituted or unsubstituted.

Salts of compounds of Formula I are the physiologically acceptable salts. Physiologically acceptable salts are particularly suitable for medical applications, due to their greater solubility in water compared with the starting or base compounds. Suitable physiologically acceptable acid addition salts of the compounds of the invention may be salts of inorganic acids such as hydrochloric acid, hydrobromic acid, phosphoric acid, and the like or of organic acids such as, for example, acetic acid, benzenesulfonic acid, methanesulfonic acid, benzoic acid, citric acid, glycolic acid, lactic acid, fumaric acid, succinic acid, adipic acid, pimelic acid, suberic acid, azelaic acid, malic acid, tartartic acid, amino acids, such as glutamic acid or aspartic acid, butanedisulfonic acid and the like.

DETAILED DESCRIPTION OF THE INVENTION

In one aspect the present invention provides a compound of Formula I

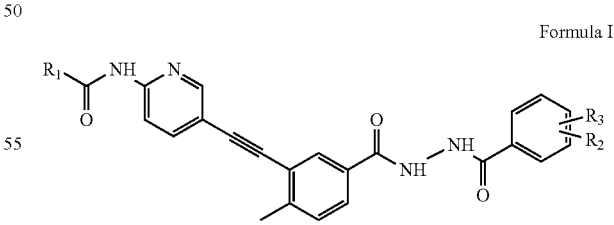

Formula I and pharmaceutically acceptable salts thereof wherein, $R_1$ is selected from —$C_{3-6}$ cycloalkyl, —$C_{1-6}$ alkyl-$NH_2$, —$C_{1-6}$ alkyl-NH($C_{1-6}$ alkyl), —$C_{1-6}$ alkyl-N($C_{1-6}$ alkyl)$_2$, —$C_{3-6}$ alkenyl, —$C_{1-6}$ alkyl, —$C_{3-6}$ alkynyl, —C(O) heterocyclyl, heterocyclyl-$C_{1-6}$ alkyl, —$C_{1-6}$ haloalkyl, —NH ($C_{3-6}$ cycloalkyl) and heterocyclyl wherein heterocyclyl is 5-6 membered non-aromatic ring containing 1 to 2 heteroatom individually selected from N, O or S;

$R_1$ is optionally substituted with one or more group independently selected from —$C_{1-4}$ alkyl, halogen, CN, NH($C_{1-6}$ alkyl), N($C_{1-6}$ alkyl)$_2$, NH$_2$ and hydroxy;

$R_2$ and $R_3$ are individually selected from a group of hydrogen, halogen, —$C_{1-4}$ alkyl, —$C_{1-4}$ haloalkyl, heterocyclyl-$C_{1-4}$ alkyl and heteroaryl wherein, heterocyclyl is 5-6 membered non-aromatic ring containing 1 to 2 heteroatom independently selected from N, O or S and is unsubstituted or substituted with —$C_{1-4}$ alkyl and heteroaryl is 5-6 membered aromatic ring containing 1 to 2 heteroatom independently selected from N, O or S and is unsubstituted or substituted with —$C_{1-4}$ alkyl.

In one embodiment, $R_1$ is —$C_{3-6}$ cycloalkyl.

In one embodiment, the compound of Formula I is selected from a group comprising:

Cyclopropanecarboxylic acid (5-{5-[N'-(2-chloro-6-methyl-benzoyl)hydrazinocarbonyl]-2-methyl-phenylethynyl}-pyridin-2-yl)amide;

N-(5-{5-[N'-(2-chloro-6-methylbenzoyl)hydrazinocarbonyl]-2-methyl-phenylethynyl}-pyridin-2-yl)-2-dimethylaminoacetamide;

N-(5-{5-[N'-(2-Chloro-6-methyl-benzoyl)hydrazinocarbonyl]-2-methyl-phenylethynyl}-pyridin-2-yl)-3-(4-methyl-piperazin-1-yl)propionamide;

N-(5-{5-[N'-(2-Chloro-6-methyl-benzoyl)hydrazinocarbonyl]-2-methyl-phenylethynyl}-pyridin-2-yl)-2-(4-dimethylaminopiperidin-1-yl)acetamide;

N-(5-{5-[N'-(2-Chloro-6-methyl-benzoyl)hydrazinocarbonyl]-2-methyl-phenylethynyl}-pyridin-2-yl)-2-(3-dimethylaminopyrrolidin-1-yl)acetamide;

N-(5-{5-[N'-(2-Chloro-6-methyl-benzoyl)hydrazinocarbonyl]-2-methyl-phenylethynyl}-pyridin-2-yl)acetamide;

Cyclopropanecarboxylic acid [5-(2-methyl-5-{N'-[4-(4-methylpiperazin-1-ylmethyl)benzoyl]-hydrazinocarbonyl}phenylethynyl)pyridin-2-yl]amide;

Cyclopropanecarboxylic acid [5-(2-methyl-5-{N'-[3-(4-methylimidazol-1-yl)-5-trifluoromethylbenzoyl]-hydrazinocarbonyl}phenylethynyl)pyridin-2-yl]amide;

1-(5-{5-[N'-(2-Chloro-6-methylbenzoyl)hydrazinocarbonyl]-2-methylphenylethynyl}-pyridin-2-yl)-3-cyclopropylurea;

N-(5-{5-[N'-(2-(Chloro-6-methylbenzoyl)hydrazinocarbonyl]-2-methylphenylethynyl}-pyridin-2-yl)-2,2,2-trifluoroacetamide;

Cyclopropanecarboxylic acid [5-(2-methyl-5-{N'-[4-(4-methylpiperazin-1-yl-methyl)-3-trifluoromethylbenzoyl]-hydrazinocarbonyl}phenylethynyl)pyridin-2-yl]amide;

N-(5-{5-[N'-(2-(Chloro-6-methylbenzoyl)hydrazinocarbonyl]-2-methylphenylethynyl}-pyridin-2-yl)butyramide;

In a preferred embodiment, the compound of Formula I is selected from a group comprising:

Cyclopropanecarboxylic acid (5-{5-[N'-(2-chloro-6-methyl-benzoyl)hydrazinocarbonyl]-2-methyl-phenylethynyl}-pyridin-2-yl)amide;

Cyclopropanecarboxylic acid [5-(2-methyl-5-{N'-[4-(4-methylpiperazin-1-ylmethyl)benzoyl]-hydrazinocarbonyl}phenylethynyl)pyridin-2-yl]amide;

Cyclopropanecarboxylic acid [5-(2-methyl-5-{N'-[3-(4-methylimidazol-1-yl)-5-trifluoromethylbenzoyl]-hydrazinocarbonyl}phenylethynyl)pyridin-2-yl]amide;

Cyclopropanecarboxylic acid [5-(2-methyl-5-[N'-[4-(4-methylpiperazin-1-yl-methyl)-3-trifluoromethylbenzoyl]-hydrazinocarbonyl]phenylethynyl)pyridin-2-yl]amide;

In one embodiment of the process for preparing compounds of the present invention, the compounds of Formula I can be prepared as per following general scheme 1

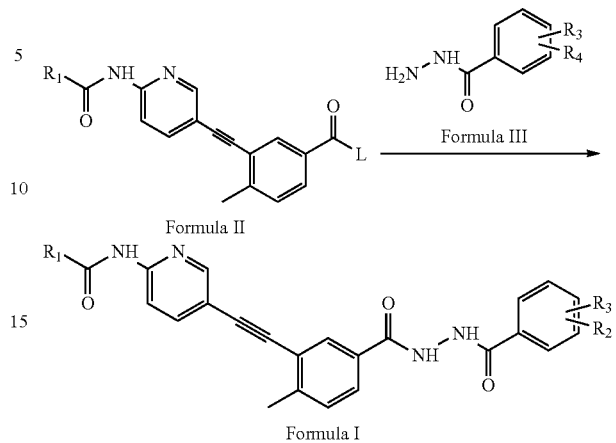

Scheme 1

The process involves condensation of the hydrazide of Formula III with the diarylacetylenic compound of Formula II, wherein $R_1$, $R_2$ & $R_3$ are as previously defined for compound of Formula I, and L is a leaving group. Preferably the condensation reaction is carried out in the presence of an inert base and/or a suitable catalyst in an inert solvent.

The compound of the Formula II in activated form (i.e. —C(O)-L) is especially an acid halide, an ester an anhydride or a cyclic imide.

The esters of Formula II can be selected from, for example vinyl esters obtainable, for example, by transesterification of a corresponding ester with vinyl acetate, carbamoylvinyl esters or by treatment with a $C_{2-5}$ alkoxyacetylene. Other active esters are of the amidino type, such as N,N'-disubstituted amidino esters (obtainable, for example, by treatment of the corresponding acid with a suitable N,N'-disubstituted carbodiimide, for example, N,N'-dicyclohexylcarbodiimide), or N,N'-disubstituted amidino esters (obtainable, for example, treatment of the corresponding acid with N,N-disubstituted cyanamide), suitable aryl esters, especially phenyl esters suitably substituted by electron-attracting substituents (obtainable, for example, by treatment of the corresponding acid with a suitably substituted phenol, for example, 4-nitrophenol, 2,4,5-trichlorophenol, or 2,3,4,5,6-pentachloro-phenol in the presence of a condensation agent, such as N,N'-dicyclohexylcarbodiimide). Other suitable active esters include cyanomethyl esters (obtainable, for example, by treatment of the corresponding acid with chloroacetonitrile in the presence of a base), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method), amino or amido esters (obtainable, for example, by treatment of the corresponding acid with an N-hydroxyamino or N-hydroxyamido compound, for example, N-hydroxysuccinimide, N-hydroxypiperidine, N-hydroxyphthalimide or 1-hydroxybenzotriazole, for example by the anhydride or carbodiimide method).

The anhydrides of the compound of Formula II may be formed with carbonic acid semiderivatives, such as corresponding esters, for example carbonic acid alkyl semiesters (obtainable, for example, by treatment of the corresponding acid with haloformic, such as chloroformic, acid); alkyl esters or with a 1-alkoxycarbonyl-2-alkoxy-1,2-dihydroquinoline, for example 1-alkoxycarbonyl-2-ethoxy-1,2-dihydroquinoline; anhydrides with dihalogenated, especially dichlorinated phosphoric acid (obtainable, for example, by treatment of the corresponding acid with phosphorus oxychloride), or anhydrides with organic acids, such as mixed anhydrides with organic carboxylic acids (obtainable, for example, by treatment of the corresponding acid with an unsubstituted or substituted acyl halide, for example, pivaloyl chloride or trifluoroacetyl chloride). Anhydrides may also be with organic sulfonic acids (obtainable, for example, by treatment of a salt, such as an alkali metal salt, of the corresponding acid, with a suitable organic sulfonic acid halide, such as alkane- or aryl-, for example methane- or p-toluenesulfonyl chloride), or with organic phosphonic acids (obtainable, for example, by treatment of the corresponding acid with a suitable organic phosphonic anhydride or phosphonic cyanide).

Suitable cyclic amides are especially amides with five-membered diazacycles of aromatic character, such as with imidazoles (obtainable, for example, by treatment of the corresponding acid with N,N'-carbonyldiimidazole; imidazolide method), or pyrazoles, for example 3,5-dimethylpyrazole.

Formula II in activated form is preferably generated in situ from the corresponding acid (i.e. when L=OH). For example, N,N'-disubstituted amidino esters can be formed in situ by reacting a mixture of the acid of Formula II (i.e. when L=OH) and the compound of Formula III in the presence of a suitable condensating agent for example N,N'-dicyclohexylcarbodiimide. Reactive mixed anhydrides of the acid may also be generated with an organic phosphonic acid in situ by reaction with propylphosphonic anhydride or diethylcyanophosphonate in the presence of suitable base for e.g. triethylamine or 4-(N,N-dimethylamino)pyridine. The reaction may be carried out in a manner known per se, the reaction conditions being dependent especially on how the acid group of Formula II has been activated, usually in the presence of a suitable solvent or diluent or of a mixture thereof and, if necessary, in the presence of a condensation agent. Customary condensation agents are, for example, carbodiimides such as N,N'-diethyl-, N,N'-diisopropyl, N,N'-dicyclohexyl- or N-ethyl-N'-(3-diethylaminopropyl)-carbodiimide; suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example, 2-ethoxy-1-ethoxycarbonyl-1,2-dihydroquinoline. The bases normally used for aiding the condensation are either inorganic bases such as sodium or potassium carbonate, or organic bases, such as pyridine, triethyamine, N,N-diisopropylethylamine or 4-(dimethylamino)pyridine.

Alternatively, the preparation of compounds of Formula I in the present invention can be performed by reacting compounds of Formula IV with the compounds of Formula V, Scheme 2, using similar condensation methods as described above (for Scheme 1); wherein $R_1$, $R_2$, $R_3$ and L are as previously defined.

Scheme 2

Formula IV

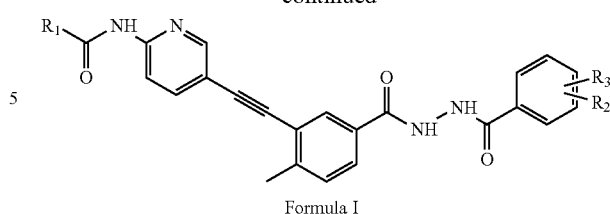

Formula I

Compounds of Formula IV can be prepared from compounds of Formula II and hydrazine of Formula IIIa, Scheme 3, utilizing the coupling procedures as described for Scheme 1, vide supra.

Scheme 3

Formula II

Formula IV

In a similar manner the compounds of Formula III can be prepared by the reaction of compounds of hydrazine hydrate and Formula V, Scheme 4.

Formula V

Formula III

The compounds of Formula II can be prepared by methods known in the literature. Suitable approaches for the preparation of the compounds for Formula II are provided in Scheme 5.

Scheme 5

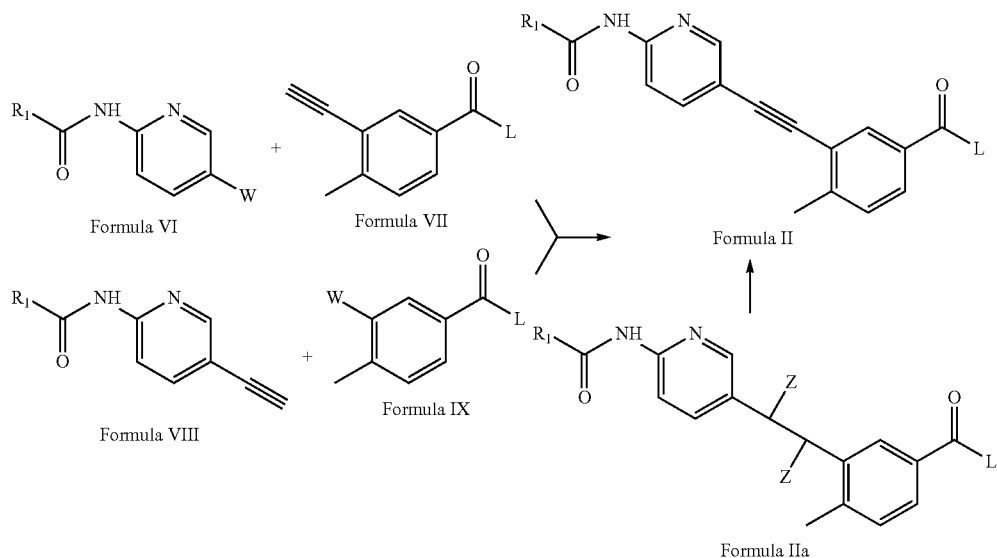

As illustrated in Scheme 5, the ethynyl moiety of pyridine of Formula VIII is coupled with phenyl ring of Formula IX, or the ethynyl moiety of phenyl ring of Formula VII is coupled with pyridine ring of Formula VI; wherein 'W' represents a leaving group like OTf, Cl, Br or I, preferably Br or I; L represent OH or O-alkyl. The coupling reaction can be performed using well known prior art methods, such as metal catalyzed coupling reactions, for example a palladium catalyzed Sonogashira coupling reaction (refer Malleron, J.-L., Fiaud, J.-C., Legros, J.-Y. Handbook of Palladium Catalyzed Organic Reactions, San Diego: Academic Press, 1997). Alternatively, the compound of Formula II is prepared from the vicinal dihalo compound of Formula IIa (where Z represents halo) by tandem dehydrohalogenations.

A strategy similar to the above can be utilized for the synthesis of compounds of Formula I as shown in Scheme 6, i.e. coupling the ethynyl moiety of pyridine ring of Formula VIII to the phenyl ring in Formula XI, or the ethynyl moiety of phenyl ring of Formula X to the pyridine ring in Formula VI; wherein W, $R_1$, $R_2$ and $R_3$ are as previously defined.

Scheme 6

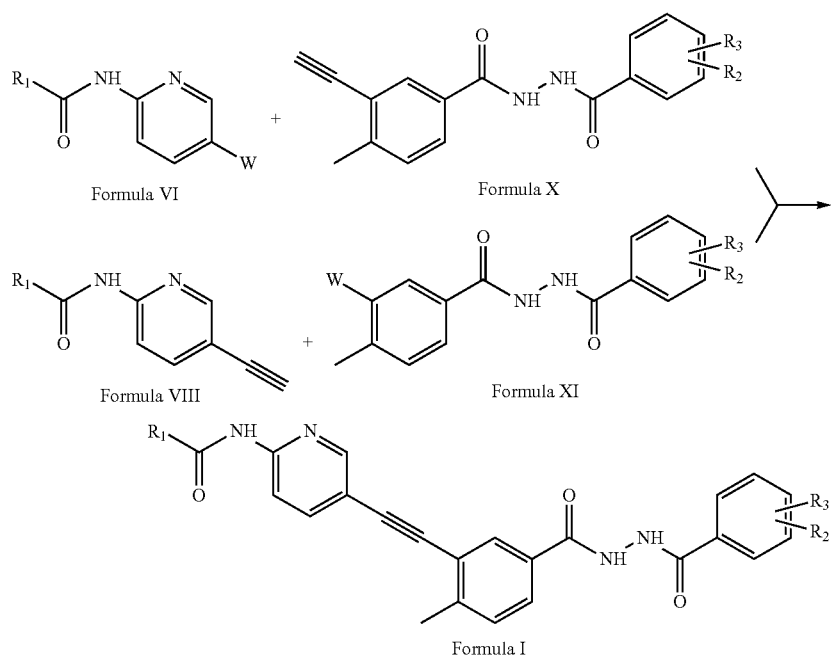

The compounds of Formula X & Formula XI can be conveniently prepared by acylation of the hydrazide of Formula III with compounds of Formula VII & Formula IX, respectively, as shown in Scheme 7; wherein L, W, X, $R_1$, $R_2$ and $R_3$ are as previously defined.

Scheme 7

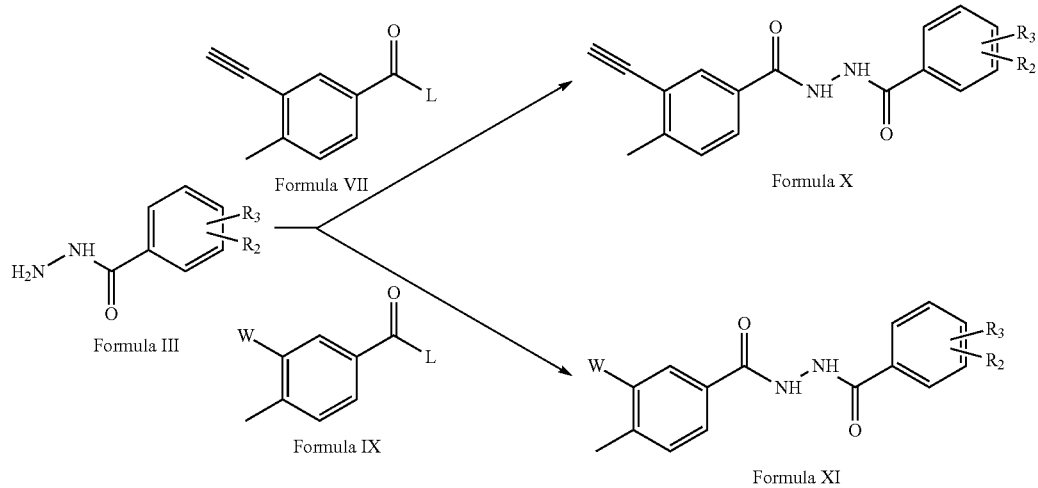

The compounds of Formula I can also be prepared by acylation of the amine of Formula XII as shown in Scheme 8.

Scheme 8

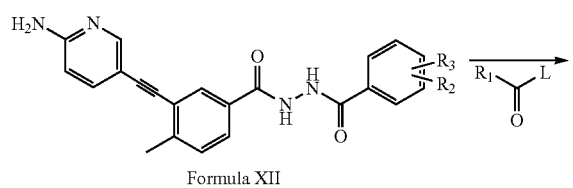

-continued

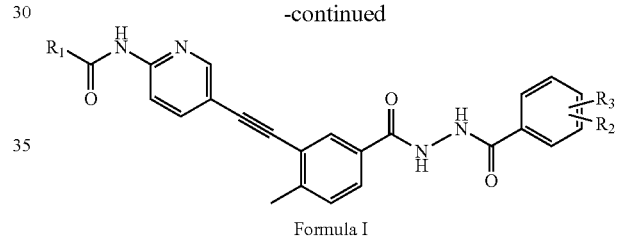

Where the above starting compounds VI, VII, VIII and IX contain functional groups that may interfere with the coupling reaction, are protected using suitable protecting groups that can be conveniently removed later.

Characterization data for some of the representative compounds of Formula I are provided in the Table-1.

TABLE 1

| Compd ID | IUPAC Name | $^1$H NMR (δ ppm) in DMSO-$d_6$ as solvent |
|---|---|---|
| I.1 | cyclopropanecarboxylic acid (5-{5-[N'-(2-chloro-6-methylbenzoyl)hydrazinocarbonyl]-2-methyl-phenylethynyl}-pyridin-2-yl)amide | 0.89 (m, 4H), 1.13-1.16 (t, 1H, J = 7.0 Hz), 2.52 (s, 3H), 2.60 (s, 3H), 7.31-7.35 (m, 1H), 7.38-7.43 (m, 2H), 7.53 (d, 1H, J = 8.0 Hz), 7.92-7.95 (m, 1H), 8.02-8.05 (m, 1H), 8.18-8.22 (m, 2H), 8.62 (m, 1H), 10.52 (s, 1H), 10.71 (s, 1H), 11.12 (s, 1H). |
| I.2 | N-(5-{5-[N'-(2-chloro-6-methyl-benzoyl)hydrazinocarbonyl]-2-methyl-phenylethynyl}-pyridin-2-yl)-2-dimethylaminoacetamide | 2.42 (s, 3H), 2.69 (s, 3H), 2.93 (s, 6H), 4.28 (br, 2H), 7.33 (m, 1H), 7.40-7.43 (m, 2H), 7.56 (d, 1H, J = 8.1 Hz), 7.60-7.68 (m, 1H), 7.95 (m, 1H), 8.14-8.18 (m, 3H), 8.69 (m, 1H), 9.99 (br, 1H), 10.53 (s, 1H), 10.72 (s, 1H), 11.46(s, 1H). |
| I.3 | N-(5-{5-[N'-(2-Chloro-6-methylbenzoyl)hydrazinocarbonyl]-2-methyl-phenylethynyl}-pyridin-2-yl)-3-(4-methyl-piperazin-1-yl)propionamide | 2.52 (s, 3H), 2.60 (s, 3H), 2.88 (s, 3H), 3.07 (m, 2H), 3.70-3.73 (m, 8H), 7.31-7.34 (m, 1H), 7.39-7.44 (m, 2H), 7.56 (d, 1H, J = 8.1 Hz), 7.95 (d, 1H, J = 8.1 Hz), 8.09 (d, 1H, J = 8.0 Hz), 8.18-8.21 (m, 2H), 8.64 (s, 1H), 10.53 (s, 1H), 10.72 (s, 1H), 11.09 (s, 1H), 11.80 (m, 2H). |
| I.4 | N-(5-{5-[N'-(2-Chloro-6-methyl-benzoyl)hydrazinocarbonyl]-2-methyl-phenylethynyl}-pyridin-2-yl)-2-(4-dimethylamino piperidin-1-yl)acetamide | 1.70-1.73 (m, 2H), 2.00 (m, 2H), 2.27-2.33 (m, 2H), 2.52 (s, 3H), 2.60 (s, 3H), 2.66 (br, 5H), 2.91-2.97 (m, 3H), 3.03-3.06 (m, 3H), 7.32-7.33 (m, 1H), 7.38-7.39 (m, 2H), 7.55 (d, 1H, J = 8.0 Hz), 7.94 (d, 1H, J = 8.0 Hz), 8.08-8.11 (m, 1H), 8.19 (s, 1H), 8.23(d, 1H, J = 8.6 Hz), 8.63 (m, 1H), 10.26 (s, 1H), 10.53 (s, 1H), 10.72(s, 1H). |

TABLE 1-continued

| Compd ID | IUPAC Name | $^1$H NMR (δ ppm) in DMSO-$d_6$ as solvent |
|---|---|---|
| I.5 | N-(5-{5-N'-(2-Chloro-6-methyl-benzoyl)hydrazine carbonyl]-2-methyl-phenyl ethynyl}-pyridin-2-yl)-2-(3-dimethylaminopyrrolidin-1-yl)acetamide | 2.55 (s, 3H), 2.61 (s, 3H), 2.72-2.86 (m, 6H), 2.93-3.00 (m, 2H), 4.10 (br, 2H), 4.43 (br, 2H), 7.32-7.38 (m, 1H), 7.40-7.43 (m, 2H), 7.56 (d, 1H, J = 8.0 Hz), 7.94-7.97 (m, 1H), 8.14-8.19 (m, 3H), 8.69 (s, 1H), 10.54 (s, 1H), 1072 (s, 1H), 11.45(s, 1H). |
| I.6 | N-(5-{5-[N'-(2-Chloro-6-methyl-benzoyl)hydrazinocarbonyl]-2-methyl-phenylethynyl}-pyridin-2-yl)acetamide | 2.18 (s, 3H), 2.52 (s, 3H), 2.60 (s, 3H), 7.33 (m, 1H), 7.40-7.41 (m, 2H), 7.55 (d, 1H, J = 8.1 Hz), 7.93-7.95 (m, 1H), 8.03-8.06 (m, 1H), 8.18-8.23 (m, 2H), 8.61 (m, 1H), 10.53 (s, 1H), 10.72 (s, 1H), 10.82 (s, 1H). |
| I.7 | Cyclopropanecarboxylic acid [5-(2-methyl-5-{N'-[4-(4-methyl-piperazin-1-ylmethyl)benzoyl]-hydrazinocarbonyl}phenyl-ethynyl)pyridin-2-yl]amide | 0.88-0.90 (m, 4H), 1.36 (m, 1H), 2.03 (m, 1H), 2.41 (br, 6H), 2.69-2.72 (m, 3H), 2.92-2.97 (m, 3H), 3.61 (br, 3H), 7.50-7.55 (m, 3H), 7.87-7.92 (m, 3H), 8.00-8.02 (m, 1H), 8.09 (s, 1H), 8.16 (d, 1H, J = 8.6 Hz), 8.58(s, 1H), 10.70 (br, 2H), 11.15 (s, 1H). |
| I.8 | Cyclopropanecarboxylic acid [5-(2-methyl-5-{N'-[3-(4-methyl-imidazol-1-yl)-5-trifluoromethyl-benzoyl]-hydrazinocarbonyl}phenyl-ethynyl)pyridin-2-yl]amide | 0.73-0.74 (m, 4H), 1.92 (m, 1H), 2.08 (s, 3H), 2.45 (s, 3H), 7.41 (d, 1H, J = 8.0 Hz), 7.62 (br, 1H), 7.77 (d, 1H, J = 7.8 Hz), 7.87-7.89 (m, 1H), 7.99 (s, 1H), 8.05 (m, 2H), 8.19 (s, 1H), 8.31(s, 2H), 8.46 (s, 1H), 10.66 (s, 1H), 10.80 (s, 1H), 10.96 (s, 1H). |
| I.9 | 1-(5-{5-[N'-(2-Chloro-6-methylbenzoyl)hydrazinocarbonyl]-2-methylphenylethynyl}-pyridin-2-yl)-3-cyclopropylurea | 0.51-0.72 (m, 4H), 2.38 (s, 3H), 2.55 (s, 3H), 3.51 (m, 1H), 7.33-7.39 (m, 3H), 7.55-7.64 (m, 2H), 7.93 (m, 3H), 8.15(s, 1H), 8.48 (s, 1H), 9.40 (s, 1H), 10.52 (s, 1H), 10.70 (s, 1H). |
| I.10 | N-(5-{5-[N'-(Chloro-6-methyl-benzoyl)hydrazinocarbonyl]-2-methylphenylethynyl}-pyridin-2-yl)-2,2,2-trifluoroacetamide | 2.52 (s, 3H), 2.62 (s, 3H), 7.33 (m, 1H), 7.40-7.41 (m, 2H), 7.57 (d, 1H, J = 9.2 Hz), 7.96 (d, 1H, J = 8.0 Hz), 8.12 (d, 1H, J = 8.6 Hz), 8.19 (s, 1H), 8.21 (s, 1H), 8.76 (s, 1H), 10.53 (s, 1H), 10.72 (s, 1H), 12.34 (s, 1H). |
| I.11 | Cyclopropanecarboxylic acid [5-(2-methyl-5-[N'-[4-(4-methyl-piperazin-1-yl-methyl)-3-trifluoro-methylbenzoyl]-hydrazino-carbonyl}phenylethynyl)pyridin-2-yl]amide | 0.89-0.90 (m, 4H), 2.09 (m, 1H), 2.23 (s, 3H), 2.38-2.51 (br, 6H), 2.61 (br, 5H), 3.22 (m, 2H), 7.56 (d, 1H, J = 8.2 Hz), 7.91-7.93 (m, 1H), 7.99 (d, 2H, J = 8.3 Hz), 8.02-8.05 (m, 1H), 8.14 (m, 1H), 8.20 (m, 1H), 8.22(m, 1H), 8.24-8.26 (m, 1H), 8.29 (m, 1H), 8.62 (m, 1H), 10.70 (s, 1H), 10.80 (s, 1H), 11.12 (s, 1H). |
| I.12 | N-(5-{5-[N'-(2-(Chloro-6-methylbenzoyl)hydrazinocarbonyl]-2-methylphenylethynyl}-pyridin-2-yl)butyramide | 0.96 (t, 3H), 1.65 (m, 2H), 2.47 (t, 2H), 2.52 (s, 3H), 2.60 (s, 3H), 7.31-7.35 (m, 1H), 7.38-7.43 (m, 2H), 7.53 (d, 1H, J = 8.1 Hz), 7.92-7.95 (m, 1H), 8.02-8.05 (m, 1H), 8.18 (m, 1H), 8.22 (m, 1H), 8.62 (m, 1H), 10.52 (s, 1H), 10.71 (s, 1H), 10.76 (s, 1H). |

The compounds of the present invention can be used to treat disorders mediated by tyrosine kinases.

The following examples serve to illustrate the invention without limiting the invention in its scope. The methods of preparing some of the starting compounds used in the examples are described as reference examples.

EXAMPLES

Example 1

Preparation of cyclopropanecarboxylic acid (5-{5-[N'-(2-chloro-6-methylbenzoyl)hydrazinocarbonyl]-2-methyl-phenylethynyl}-pyridin-2-yl)amide (Formula I.1)

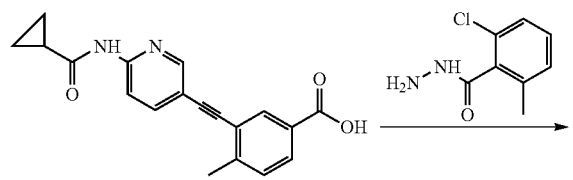

-continued

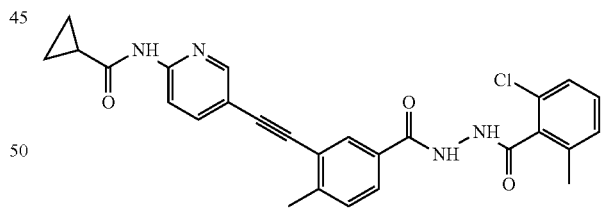

A mixture of 3-({6-[(cyclopropylcarbonyl)amino]pyridin-3-yl}ethynyl)-4-methylbenzoic acid, N-(3-dimethylaminopropyl)-N'-ethylcarbodiimide hydrochloride and 1-hydroxybenzotriazole in N,N-dimethylformamide was stirred at ambient temperature for 1 hr. 2-chloro-6-methylbenzohydrazide was added and the mixture stirred for 12 hrs at ambient temperature. Concentration and trituration of the residue with water produced a solid which was filtered, washed with water and finally dried in vacuo to get a white solid.

Example 2

N-(5-{5-[N'-(2-chloro-6-methylbenzoyl)hydrazinocarbonyl]-2-methyl-phenylethynyl}-pyridin-2-yl)-2-dimethylaminoacetamide (Formula I.2)

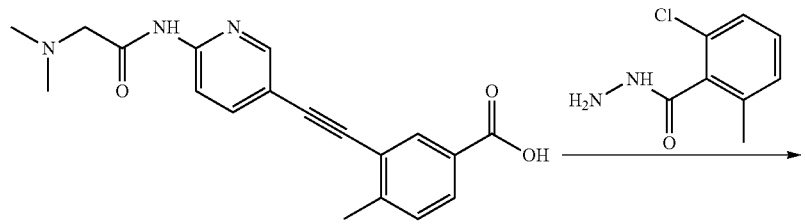

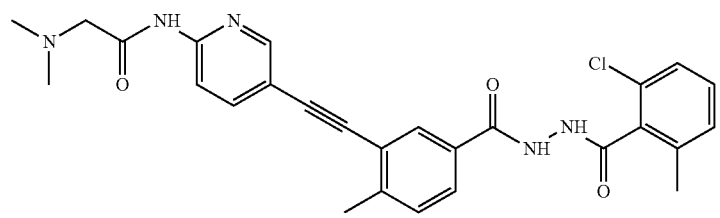

Starting from 3-[(6-{[(dimethylamino)acetyl]amino}pyridin-3-yl)ethynyl]-4-methylbenzoic acid the compound of Formula I.2 was prepared by the process disclosed in example 1.

Example 3

N-(5-{5-[N'-(2-Chloro-6-methylbenzoyl)hydrazinocarbonyl]-2-methyl-phenylethynyl}-pyridin-2-yl)-3-(4-methyl-piperazin-1-yl)propionamide (Formula I.3)

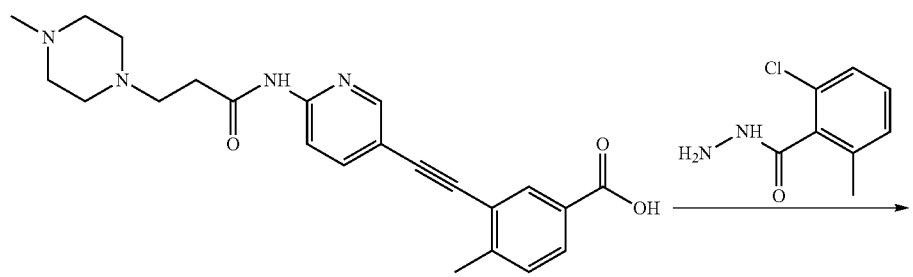

Formula II-3

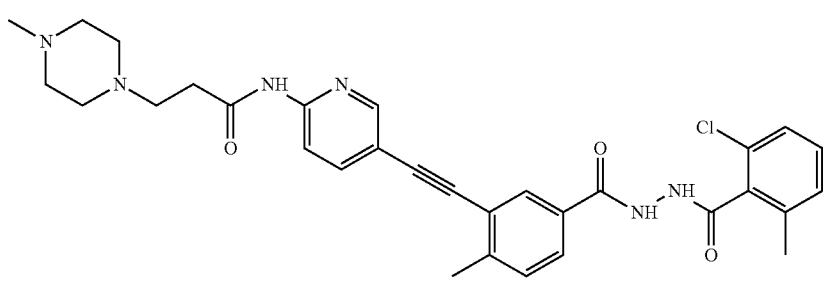

Starting from compound of Formula II-3, the compound of Formula I.3 was prepared by the process disclosed in example 1.

Example 4

N-(5-{5-[N'-(2-Chloro-6-methyl-benzoyl)hydrazinocarbonyl]-2-methyl-phenylethynyl}-pyridin-2-yl)-2-(4-dimethylaminopiperidin-1-yl)acetamide (Formula I.4)

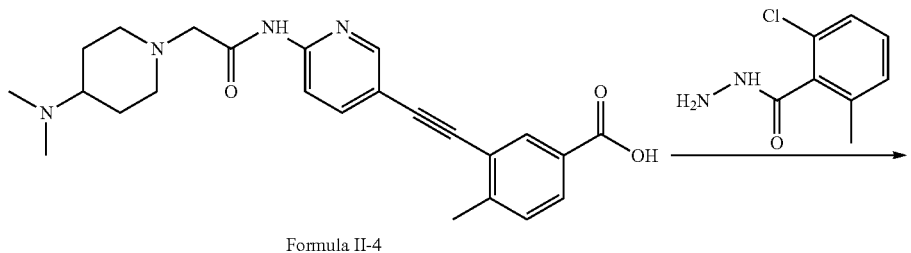

Formula II-4

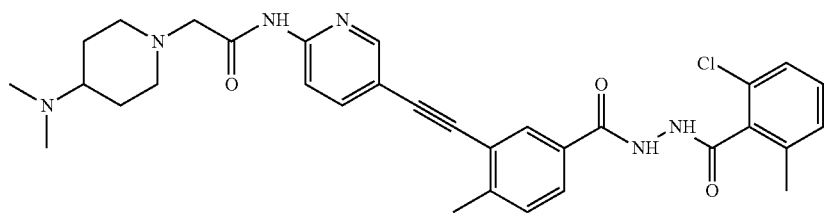

Starting from compound of Formula II-4, the compound of Formula I.4 was prepared by the process disclosed in example 1.

Example 5

N-(5-{5-[N'-(2-Chloro-6-methyl-benzoyl)hydrazinocarbonyl]-2-methyl-phenylethynyl}-pyridin-2-yl)-2-(3-dimethylaminopyrrolidin-1-yl)acetamide (Formula I.5)

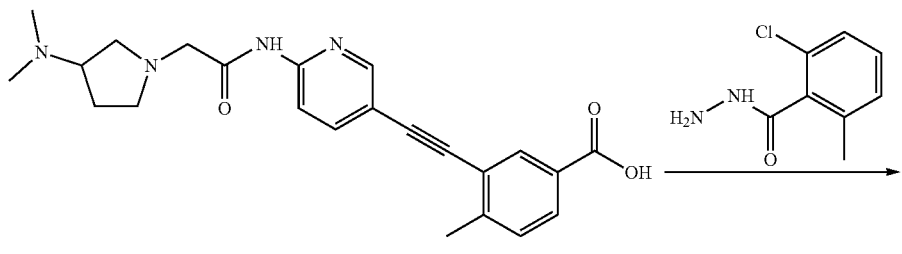

Formula II-5

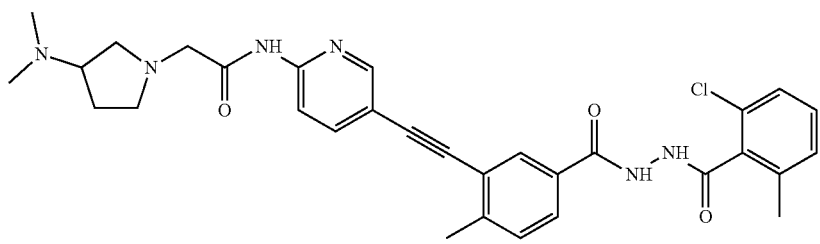

Starting from compound of Formula II-5, the compound of Formula I.5 was prepared by the process disclosed in example 1.

Example 6

N-(5-{5-[N'-(2-Chloro-6-methyl-benzoyl)hydrazinocarbonyl]-2-methyl-phenylethynyl}-pyridin-2-yl)acetamide (Formula I.6)

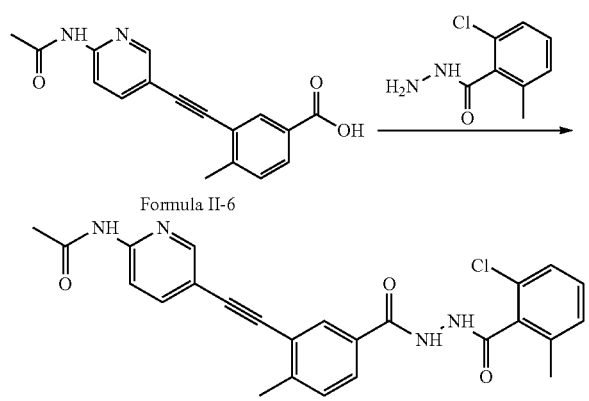

Starting from 3-{[6-(acetylamino)pyridin-3-yl]ethynyl}-4-methylbenzoic acid, the compound of Formula I.6 was prepared by the process disclosed in example 1.

Example 7

1-(5-{5-[N'-(2-Chloro-6-methyl-benzoyl)-hydrazinocarbonyl]-2-methyl-phenylethynyl}-pyridin-2-yl)-3-cyclopropylurea (I.9)

A solution of 2-amino-5-iodopyridine in DMF was added to a stirred mixture of diphenylphosphoryl azide, cyclopropane carboxylic acid and triethyl amine in toluene at 25 to 30° C. and stirred at 120-125° C. for 3 hrs. The reaction mixture was concentrated and the crude product was purified by flash chromatography on silica gel (elution with 20% ethyl acetate in hexane) to provide 1-cyclopropyl-3-(5-iodopyridin-2-yl) urea.

A mixture of 2-chloro-6-methylbenzoic acid N'-(3-ethynyl-4-methyl benzoyl) hydrazide, 1-cyclopropyl-3-(5-iodopyridin-2-yl)urea, $Pd(Pd)_2Cl_2$, CuI and triethylamine in DMF was heated at 90° C. for 16 hrs under nitrogen atmosphere. The reaction mixture was concentrated and the crude product was purified by flash chromatography on silica gel (elution with 2% Methanol in MDC) to provide the title compound.

Pharmacological Activity
In-vitro Cell Proliferation Assay

K562/U937 cells (2×104 per well) were incubated with the test compounds/vehicle in a total volume of 200 μL of media at 37° C. with 5% CO2. On day 4, 20 μL MTT 5 mg/ml was added and the cells were incubated for 4-5 hours followed by addition of 100 μL of 10% SDS prepared in 0.06N HCl. The cells were incubated overnight at 37° C. with 5% CO2. On Day 5 the optical density was measured at 570 nm with 630 nm as reference wavelength. The optical density in the vehicle treated wells was compared with that of the test compound treated wells.

Results for the representative compounds of Formula I are provided in Table-2.

TABLE 2

| Compd. | c-Abl kinase (K562 cells); % Inhibition | | |
|---|---|---|---|
| ID | 100 nM | 10 nM | 1 nM |
| I.1 | 87.0 | 91.1 | 84.7 |
| I.2 | 82.9 | 82.5 | 71.6 |
| I.3 | 87.9 | 85.5 | 75.0 |
| I.4 | 86.9 | 81.4 | 76.5 |
| I.5 | 82.1 | 81.7 | 71.4 |
| I.6 | 91.0 | 91.6 | 88.4 |
| I.7 | 85.9 | 78.6 | 24.6 |
| I.8 | 86.1 | 84.0 | 68.9 |
| I.9 | 87.8 | 83.6 | 61.0 |
| I.10 | 73.3 | 78.5 | 39.8 |
| I.11 | 57.2 | 58.3 | 54.0 |
| I.12 | ND | 80.6 | 33.6 |

ND: Not determined

Mutated Abl (T315I) (Human)Kinase

In a final reaction volume of 25 μL, mutated Abl (T315I) (human) (5-10 mU) is incubated with 8 mM MOPS pH7.0, 0.2 mM EDTA, 5004 EAIYAAPFAKKK, 10 mM Mg(OAc)2 and [γ-33P-ATP] [specific activity approx. 500 cpm/pmol, concentration as required]. The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

The compounds of Formula I showed good inhibitory action on the mutated Abl T315I cell line. Activity data on the mutated Abl T315I cell line for some representative compound is provided in Table-3.

TABLE 3

| Compd. | Abl-T315I % Inhibition | |
|---|---|---|
| ID | 30 nM | 3 nM |
| I.1 | 98.0 | 87.0 |
| I.2 | 87.0 | 50.0 |
| I.3 | 94.0 | 59.0 |
| I.4 | 95.0 | 70.0 |
| I.5 | 96.0 | 66.0 |
| I.6 | 89.0 | 68.0 |

The invention claimed is:
1. A compound of Formula I

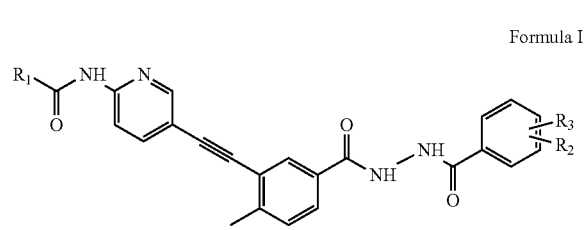

Formula I or a pharmaceutically acceptable salt thereof wherein,
$R_1$ is selected from —$C_{3-6}$ cycloalkyl, —$C_{1-6}$ alkyl-$NH_2$, —$C_{1-6}$ alkyl-$NH(C_{1-6}$ alkyl), —$C_{1-6}$ alkyl-$N(C_{1-6}$ alkyl)$_2$, —C$_{3-6}$ alkenyl, —C$_{3-6}$ alkynyl, —C$_{1-6}$ alkyl, —C$_{1-6}$ haloalkyl, and —NH(C$_{3-6}$ cycloalkyl);

R$_1$ is optionally substituted with one or more group independently selected from the group consisting of —C$_{1-4}$ alkyl, halogen, CN, NH(C$_{1-6}$ alkyl), N(C$_{1-6}$ alkyl)$_2$, NH$_2$ and hydroxy;

R$_2$ and R$_3$ are individually selected from a group of hydrogen, halogen, —C$_{1-4}$ alkyl, and —C$_{1-4}$ haloalkyl.

2. The compound of Formula I of claim 1 wherein, R$_1$ is —C$_{3-6}$ cycloalkyl; and R$_2$ and R$_3$ are independently selected from a group consisting of hydrogen, halogen, —C$_{1-4}$ alkyl and —C$_{1-4}$ haloalkyl.

3. The compound of Formula I as in claim 1 selected from the group consisting of:

Cyclopropanecarboxylic acid (5-{5-[N'-(2-chloro-6-methylbenzoyl)hydrazinocarbonyl]-2-methyl-phenylethynyl}-pyridin-2-yl)amide;

N-(5-{5-[N'-(2-chloro-6-methylbenzoyl)hydrazinocarbonyl]-2-methyl-phenylethynyl}-pyridin-2-yl)-2-dimethylaminoacetamide;

N-(5-{5-[N'-(2-Chloro-6-methyl-benzoyl)hydrazinocarbonyl]-2-methyl-phenylethynyl}-pyridin-2-yl)acetamide;

Cyclopropanecarboxylic acid [5-(2-methyl-5-{N'-[3-(4-methylimidazol-1-yl)-5-trifluoromethylbenzoyl]-hydrazinocarbonyl}phenylethynyl)pyridin-2-yl]amide;

1-(5-{5-[N'-(2-Chloro-6-methylbenzoyl)hydrazinocarbonyl]-2-methylphenylethynyl}-pyridin-2-yl)-3-cyclopropylurea;

N-(5-{5-[N'-(2-(Chloro-6-methylbenzoyl)hydrazinocarbonyl]-2-methylphenylethynyl}-pyridin-2-yl)-2,2,2-trifluoroacetamide; and N-(5-{5-[N'-(2-(Chloro-6-methylbenzoyl)hydrazinocarbonyl]-2-methylphenylethynyl}-pyridin-2-yl)butyramide.

4. The compound of Formula I of claim 3, wherein the compound is cyclopropanecarboxylic acid (5-{5-[N'-(2-chloro-6-methylbenzoyl)hydrazinocarbonyl]-2-methyl-phenylethynyl}-pyridin-2-yl)amide.

* * * * *

UNITED STATES PATENT AND TRADEMARK OFFICE
CERTIFICATE OF CORRECTION

PATENT NO. : 10,150,733 B2
APPLICATION NO. : 15/574967
DATED : December 11, 2018
INVENTOR(S) : Hemant Ashvinbhai Chokshi et al.

It is certified that error appears in the above-identified patent and that said Letters Patent is hereby corrected as shown below:

In the Claims

In Claim 3, Column 22, Line 4:
Delete "Cyclopropanecarboxylic acid [5-(2-methyl-5-{N'-[3-(4-methylimidazol-1-yl)-5-trifluoromethylbenzoyl]-hydrazinocarbonyl}phenylethynyl)pyridin-2-yl]amide"

Signed and Sealed this
Twenty-ninth Day of October, 2019

Andrei Iancu
*Director of the United States Patent and Trademark Office*